US00PP11418P

United States Patent [19]

McNicol et al.

[11] Patent Number: Plant 11,418

[45] Date of Patent: Jun. 13, 2000

[54] RASPBERRY PLANT NAMED 'GLEN AMPLE'

[75] Inventors: Ronnie J. McNicol, Dundee; Derek L. Jennings, Kent, both of United Kingdom

[73] Assignee: Scottish Crop Research Institute, Dundee, United Kingdom

[21] Appl. No.: 09/069,762

[22] Filed: Apr. 30, 1998

[51] Int. Cl.[7] ..... A01H 5/00

[52] U.S. Cl. ..... Plt./204

[58] Field of Search ..... Plt./204

[56] References Cited

U.S. PATENT DOCUMENTS

P.P. 4,485 11/1979 Reiter ..... Plt./204
P.P. 4,486 11/1979 Reiter ..... Plt./204

OTHER PUBLICATIONS

Moore, P.P., "Variation in Drupelet Number and Weight in Pacific Northwest Red Raspberries" Fruit Varieties Journal 1998 vol. 52, No. 2, pp. 103–106.

Elliott, Charles "The Berry Man" Horticulture v. 95 No. 7 Jul./Aug. '98 p. 28.

*Primary Examiner*—Howard J. Locker
*Assistant Examiner*—Wendy A. Baker
*Attorney, Agent, or Firm*—Burns, Doane, Swecker & Mathis, L.L.P.

[57] ABSTRACT

The new and distinct cultivar of raspberry (i.e., *Rubus idaeus* L.) is provided. The cultivar forms attractive large bright red berries of good flavor in exceptionally high yields on long fruiting laterals. The drupelet cohesion tends to be somewhat reduced when the plant is grown in cooler climates (e.g., Scotland). The plant exhibits a spine-free very upright growth habit of good vigor. The berries are suitable for consumption as high grade fresh fruit and also are amenable to processing. Additionally, the plant has displayed resistance to *Amphorophora idaei* aphid virus vector.

4 Drawing Sheets

SUMMARY OF THE INVENTION

The instant plant (i.e., *Rubus idaeus* L.) was created in the course of a planned breeding program carried out in 1978 at the Scottish Crop Research Institute located at Invergowrie, Dundee, Scotland, United Kingdom. The parents used to make the cross were unnamed selections of the Scottish Crop Research Institute and were designated 'SCRI 7326E1' and 'SCRI 7412H16'. Neither parent is patented in the United States. The parentage of the new cultivar can be expressed as follows:

'SCRI 7326E1'×'SCRI 7412H16'.

The parentage of the new cultivar included the 'Glen Prosen' cultivar (non-patented in the United States) and the 'Meeker' cultivar (non-patented in the United States. A sister seedling from the same cross created the 'Glen Rosa' cultivar (non-patented in the United States).

The original plant of the new cultivar was selected during 1981 from the resulting plants and was found to exhibit:

(a) a spine-free very upright growth habit of good vigor, (b) the ability to form attractive large red fruit of good flavor in exceptionally high yields on long fruiting laterals, and (c) resistance to *Amphorophora idaei* aphid virus vector.

When compared to the sister 'Glen Rosa' cultivar, the new cultivar of the present invention is found to form larger less firm fruit in higher yields as reported hereafter. Also, when compared to 'Glen Clova' cultivar (non-patented in the United States), the new cultivar exhibits larger, deeper red fruit in higher yields as reported hereafter, a later picking date (i.e., commonly approximately 7 to 8 days later), and a longer picking period.

The new cultivar has been asexually reproduced by cuttings at the Scottish Crop Research Institute, Dundee, Scotland, United Kingdom. Such asexual reproduction has demonstrated that the characteristics of the new cultivar are stable and are transmitted without change through succeeding propagations.

The new cultivar of the present invention initially was designated 7815B8 and subsequently has been named 'Glen Ample'.

The performance of the new 'Glen Ample' cultivar has been tested and evaluated during 1989 to 1993 at Brogdale Horticultural Trust, Faversham, Kent, United Kingdom, and elsewhere. Representative fruit data obtained when comparing the new cultivar with other cultivars is reported hereafter.

| Cultivar | Marketable Berry Yield (tonnes/ha) | Unmarketable Berry Yield (tonnes/ha) | Total Yield (tonnes/ha) | Average Berry Weight (g) |
|---|---|---|---|---|
| 'Glen Ample' | 17.6 | 4.4 | 22.0 | 3.9 |
| 'Glen Rosa' | 12.4 | 5.0 | 17.4 | 2.9 |
| 'Glen Shee' | 9.7 | 5.9 | 15.6 | 4.5 |
| 'Glen Clova' | 9.1 | 4.1 | 13.2 | 2.6 |
| 'Leo' | 9.3 | 3.5 | 12.8 | 3.1 |

It will be noted that the berries of the new cultivar commonly weigh approximately 4 grams. However, fruit of the new cultivar weighing up to approximately 6 grams sometimes is observed.

The above data demonstrates the exceptionally high fruit yield made possible by the new 'Glen Ample' cultivar. The berries are suitable for consumption as high grade fresh fruit and also are well suited for processing. Canned and frozen products can be formed which are believed to be comparable to those of the 'Glen Clova' cultivar.

When the new cultivar is grown in cooler climates (e.g., in Scotland) the drupelet cohesion of the fruit has been observed to be somewhat diminished. The fruit of the new cultivar tends to be less firm than that of its sister 'Glen Rosa' cultivar as previously indicated.

BRIEF DESCRIPTION OF THE PHOTOGRAPHS

The accompanying photographs show typical specimens of the new cultivar in color as true as is reasonably possible to make the same in color illustrations of this character. The photographs were prepared on Jul. 31, 1995 and depict three year-old plants and plant parts derived therefrom which were grown outdoors at the Scottish Crop Research Institute located at Dundee, Scotland, United Kingdom.

DETAILED DESCRIPTION

The following is a detailed description of the new 'Glen Ample' raspberry cultivar. The specimens described were grown at the Scottish Crop Research Institute located at Invergowrie, Dundee, Scotland, United Kingdom. Color designations are presented with reference to the R.H.S. Colour Chart of The Royal Horticultural Society, London, United Kingdom, except where common color terms are used which are to be accorded their ordinary color significance.

PLANT AND FOLIAGE

Figure 1:
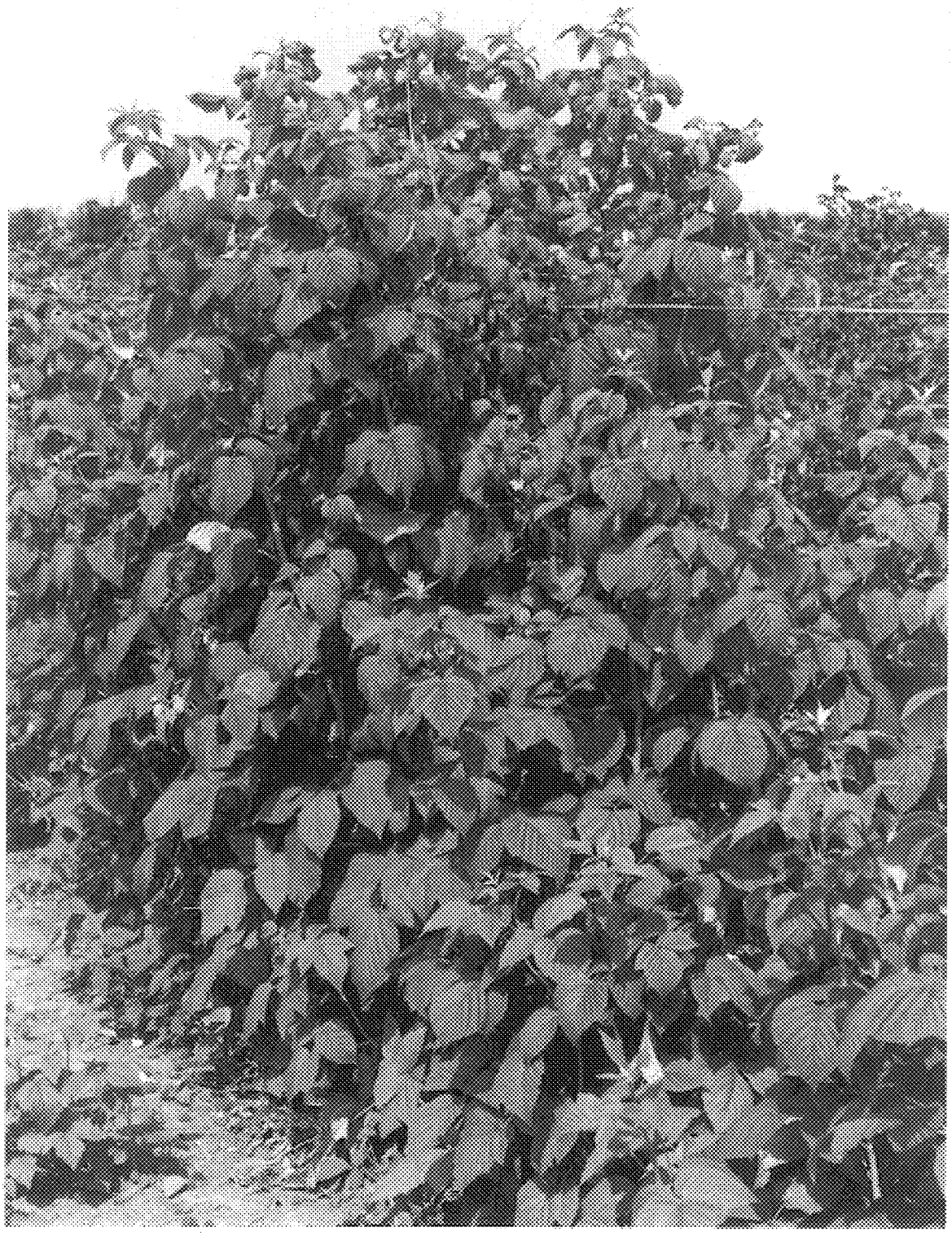
FIG. 1 illustrates overall fruited plants of the new cultivar wherein the very upright plant growth habit is depicted. The fruiting laterals are shown to be long and very upright.
Figure 2:
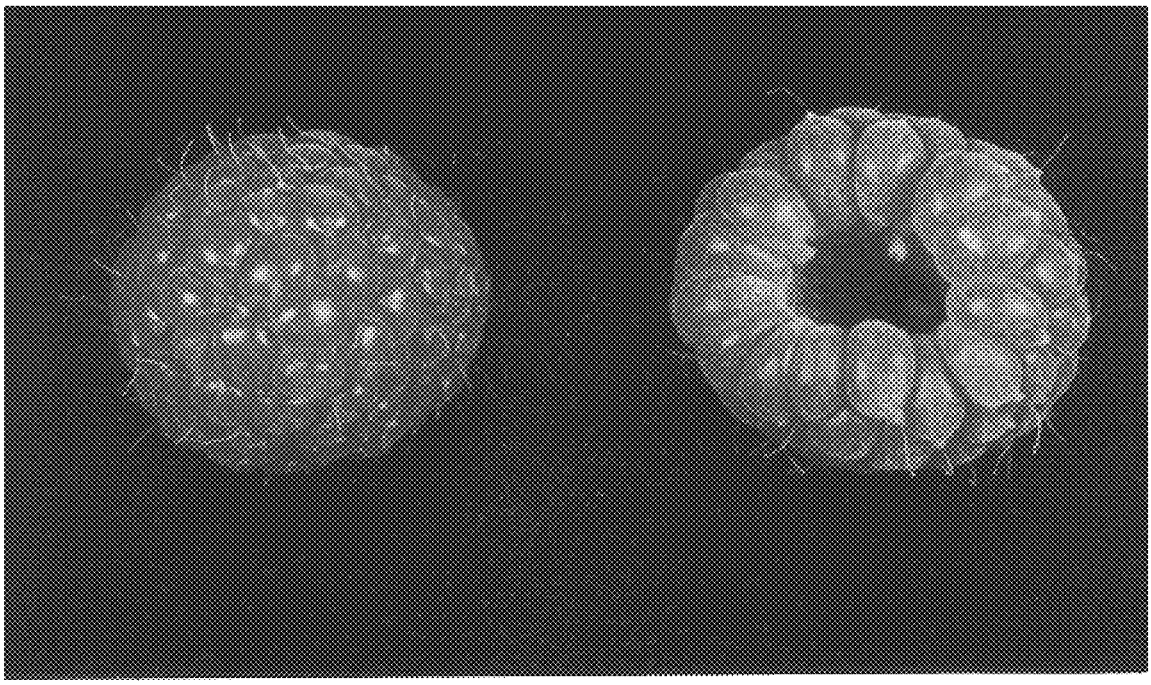
FIG. 2 illustrates enlarged close-up end views of typical large fleshy fruit of the new cultivar.
Figure 3:
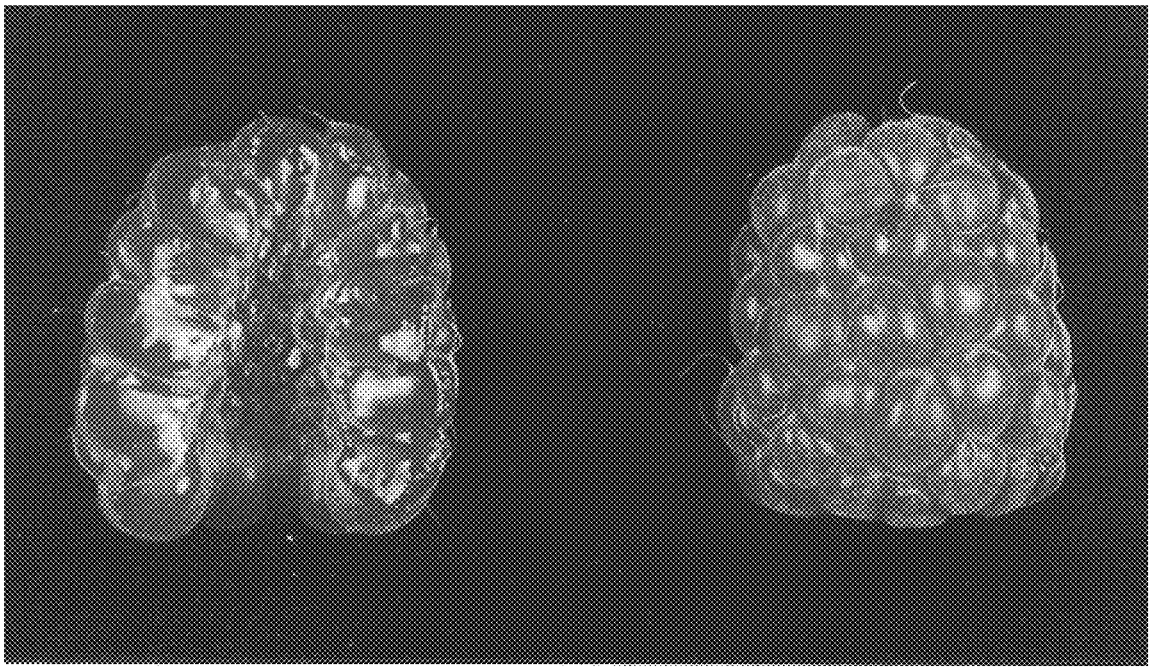
FIG. 3 illustrates enlarged close-up side views of typical large fleshy fruit of the new cultivar. Some of the drupelets have been removed from the fruit on the left so as to provide an unobstructed view of the interior portion of the fruit.
Figure 4:
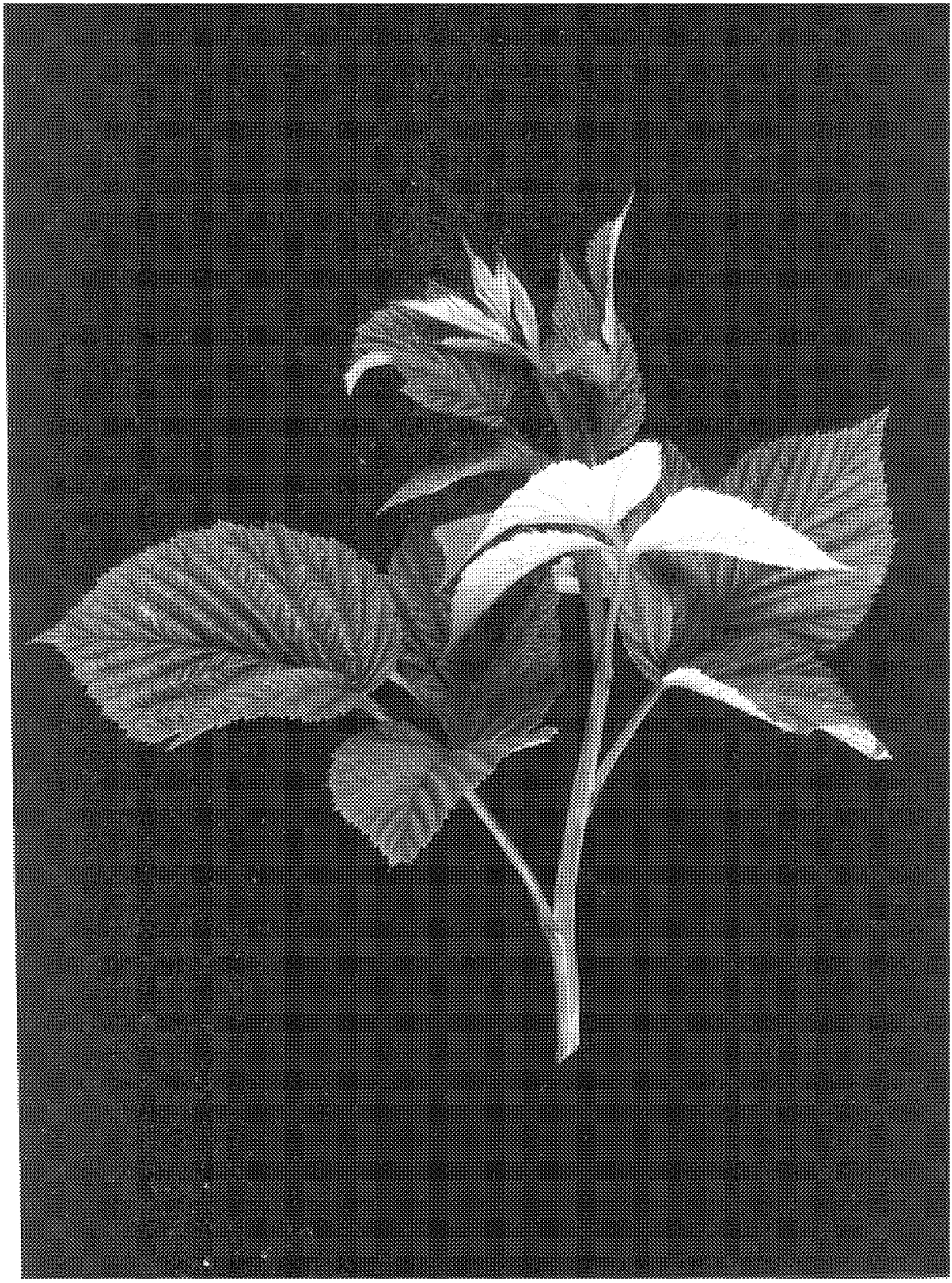
FIG. 4 illustrates a tip of growing foliage of the new cultivar from a floricane wherein the leaflets are in various stages of development.
Figure 5:
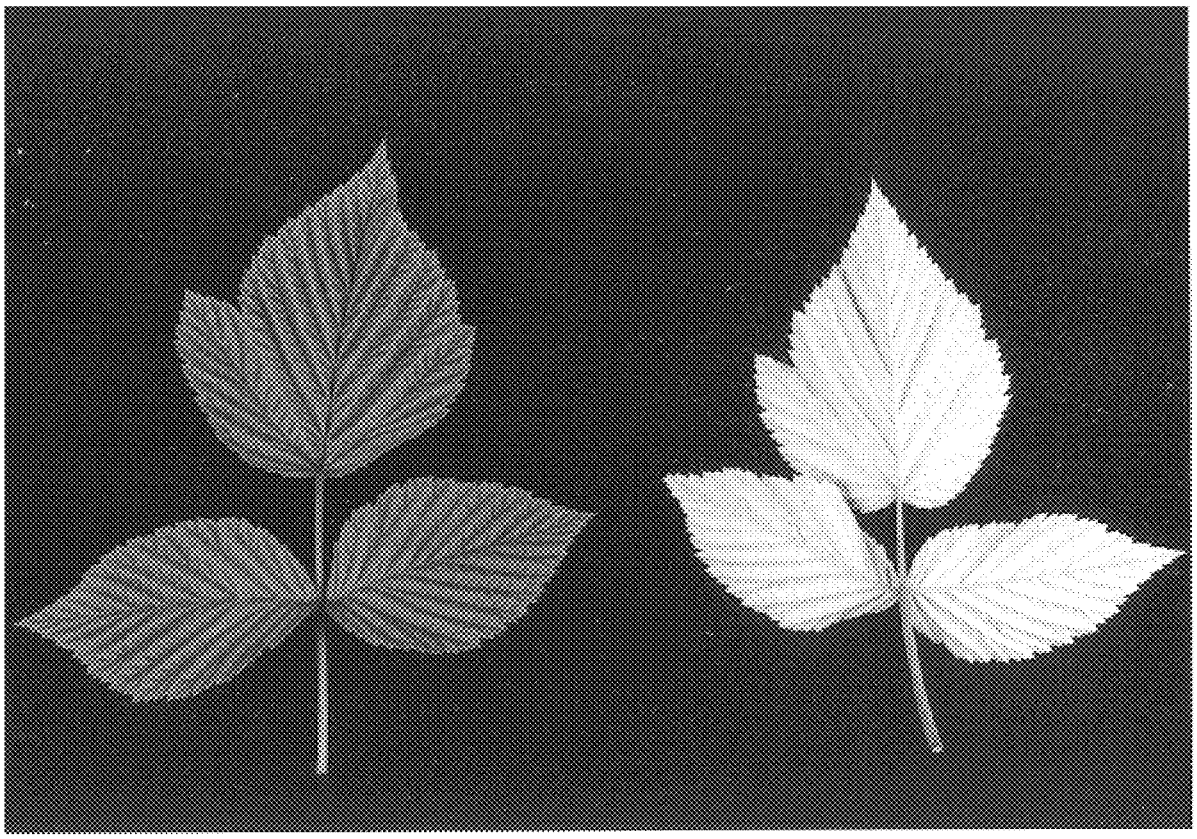
FIG. 5 illustrates fully opened leaflets of the new cultivar from a floricane with the upper surface being shown at the left and the under surface at the right.

The plant exhibits a very upright growth habit as illustrated in FIG. 1. Typical mature plant heights commonly are approximately 165 to 195 cm. (e.g., 175 cm.) and vary with the growing conditions that are encountered. Good vigor is exhibited. Spines are absent on the new canes as well as on those from the previous season. The canes are upright with a somewhat sparse leaf presentation, and are a typical brown coloration during the winter. The fruit is borne primarily upon the previous year's growth. The somewhat sparse leaf coverage tends to provide an excellent fruit presentation at harvest time. The leaves are crinkled, concave, and moderately glossy as illustrated in FIGS. 4 and 5. New shoots commonly possess some anthocyanin coloration (Red Group 46A). The number of leaflets per internode tends to be five on the middle and lower portions of the cane. On the upper portions of the cane there is a predominance of three leaflets per internode. The leaflets formed on primocanes tend to posses a greater length-to-width ratio than the leaflets formed on floricanes. For instance, a primocane typically forms a terminal leaflet that exhibits a length of approximately 11 cm. and a width of approximately 6.1 cm., and side leaflets having a length of approximately 10.5 cm. and a width of approximately 5 cm. This can be compared to leaflets of floricanes having a length of approximately 10 cm. and a width of approximately 9 cm. The leaflets on the upper surfaces are medium green in coloration (e.g., approaching Yellow-Green Group 146B) as illustrated in FIGS. 4 and 5. On the under surfaces the leaflets are considerably lighter and approach Greyed-Green Group 193B in coloration (as illustrated). The floricane coloration is near Greyed-Orange Group 165A and the primocane coloration is near Red Group 46A. The internodal distance commonly is approximately 6 to 8 cm. and is highly dependent upon the nutrient, water, and the climatic conditions that are encountered.

INFLORESCENCE

White flowers (near White Group 155A) are borne on short slender pedicels which lack spines. The time of bloom is mid-season for a summer-fruiting raspberry. The flowers have five petals with the pedicel commonly having a length of approximately 4 to 5 cm. However, the more basal the pedicel the longer it commonly becomes with pedicel lengths up to about 9 cm. then being observed. A typical flower diameter is approximately 2.2 cm. The flowers predominantly are borne singly, and sometimes in clusters of two or more. Terminal branch flower clusters frequently may consist of two flowers and basal flower clusters may number three to five. The flowers have no discernable fragrance.

HARVEST TIME

The 50 percent picking date commonly is approximately 7 to 8 days later than that of the 'Glen Clova' cultivar. Also, the harvest period commonly is longer for the new 'Glen Ample' cultivar. At more southerly growing areas, the 50 percent picking date may be up to approximately 10 days later than that of the 'Glen Cova' cultivar. At Dundee, Scotland, United Kingdom, a typical date to start picking for the new cultivar is July $12^{th}$, a typical date for 50 percent picking is July $21^{st}$, and typical date to end picking is August $6^{th}$. At Brogdale Horitcultural Trust, Faversham, Kent, United Kingdom a typical date to start picking for the new cultivar is June $24^{th}$, a typical date for 50 percent picking is July $13^{th}$, and a typical date to end picking is July $31^{st}$.

FRUIT

As indicated, the attractive berries formed on the new cultivar are large in size. Fifty frozen berries produced at the Scottish Crop Research Institute during 1997 exhibited an average length of 23.24 mm. and an average width of 22.34 mm. The fruit is round conical in configuration (as illustrated) and is bright in appearance with a low to mid-level of glossiness. The berries are firm and fleshy and of good taste. The drupelet cohesion tends to be reduced somewhat when grown in cooler climates. The berries commonly weigh on the order of 4 grams; however, some fruit of 6 grams is commonly observed. The number of drupelets per fruit commonly is approximately 93. Typical fruit Brix levels are approximately 10.5 percent. The typical shelf life commonly is approximately 6 to 8 days when stored at 2° C. and is superior to other varieties presently available in the United Kingdom. For instance, once picked the fruit often can be stored for up to six days prior to sale plus an additional two days prior to consumption by the consumer. The berry coloration typically approaches Red Group 43A to 43B.

DISEASE RESISTANCE

Resistance a strain of aphid virus vector (i.e., *Amphorophora idaei*) has been observed to date. However, susceptibility to raspberry bushy dwarf virus (RBDV) has been encountered.

I claim:

1. A new and distinct variety of raspberry plant having the following combination of characteristics:

(a) exhibits a spine-free very upright growth habit of good vigor, (b) the ability to form attractive large red fruit of good flavor in exceptionally high yields on long fruiting laterals, and (c) exhibits resistance to *Amphorophora idaei* aphid virus vector;

substantially as illustrated and described.

* * * * *